United States Patent [19]

Gröner et al.

[11] Patent Number: 4,789,632
[45] Date of Patent: Dec. 6, 1988

[54] PROCESS FOR GROWING GRANULOSIS VIRUSES

[75] Inventors: Albrecht Gröner, Seeheim-Jugenheim; Werner Knauf, Eppstein/Taunus, both of Fed. Rep. of Germany

[73] Assignee: Hoechst Aktiengesellschaft, Frankfurt am Main, Fed. Rep. of Germany

[21] Appl. No.: 84,284

[22] Filed: Aug. 11, 1987

[30] Foreign Application Priority Data

Aug. 13, 1986 [DE] Fed. Rep. of Germany ....... 3627396

[51] Int. Cl.$^4$ ............................................. C12N 7/00
[52] U.S. Cl. .................................... 435/235; 435/237
[58] Field of Search ........................................ 435/235

[56] References Cited
PUBLICATIONS

Miltenburger et al.–Chem. Abst. vol. 101 (1984) pp. 226, 639f.
Tanada, Y: J. Insect Pathol. 6, 378, 1984.
Huber, Mitt. Dtsch. Ges. allg. angew. Ent. 4, 55, 1983.
Huber, J.: Mitt. Dtsch. Ges. allg. angew. Ent. 2, 141, 1981.
Glen, D. M. & Payne, C. C.: Ann. appl. Biol. 104, 87, 1984.
H. G. Miltenburger et al., "The Cellular Substrate: A Very Important Requirement For Baculovirus In Vitro Replication", *Z. Naturfotsch., C. Biosci.*, 39 C(9–10), 993–1002 (1984).

*Primary Examiner*—Sam Rosen
*Attorney, Agent, or Firm*—Curtis, Morris & Safford

[57] ABSTRACT

The invention relates to a process for growing *Cydia pomonella* granulosis virus (CpGV), which comprises propagating the virus in Larvae of Tortricidae species which have a LD$_{50}$ for this virus which is a factor of 5 to 100,000 higher than that of codling moth Larvae.

5 Claims, No Drawings

PROCESS FOR GROWING GRANULOSIS VIRUSES

After oral intake by sensitive insect larvae, granulosis viruses, which belong to the family Baculoviridae, multiply in various organs and tissues of these insects. Cytopathogenic effects result in the death of the insect larvae.

The granulosis virus of the codling moth (Cydia(=-Laspeyresia=Carpocapsa) pomonella L., from the family of Tortricidae) was isolated from codling moth larvae in Berkeley, Calif., in 1963 (TANADA, Y.: J.Insect Pathol. 6, 378, 1984). Its short name is "CpGV". CpGV is outstandingly suitable for the selective control of the codling moth within the framework of integrated plant protection in fruit crops (HUBER, Mitt. Dtsch. Ges. allg. angew. Ent. 4, 55, 1983).

The production of CpGV in codling moth larvae takes place by infection of the larvae in the final larval stage with the granulosis virus followed by extraction of the viruses from the larval cadavers (for example: HUBER, J.: Mitt. Dtsch. Ges. allg. angew. Ent. 2, 141, 1981; GLEN, D.M. & PAYNE, C.C.: Ann. appl. Biol. 104. 87, 1984).

Because of the very great virulence of CpGV for codling moth larvae, mass propagation of the codling moth must take place under semisterile conditions in order to prevent infestation of the propagation batches with CpGV. This semisterile propagation is very labor- and cost-intensive.

It has now been found, surprisingly, that it is possible in an advantageous manner to produce CpGV in other Tortricidae species too.

Hence the present invention relates to a process for growing Cydia pomonella granulosis virus, which comprises propagating the virus in larvae of Tortricidae species which have a $LD_{50}$ for this virus which is a factor of 5 to 100,000, preferably 10 to 5,000, higher than that of codling moth larvae.

The process is preferably carried out in larvae of the subfamily Olethreutinae, for example in larvae of Grapholita molesta, Rhyacionia buoliana, Cydia nigricana or Cryptophlebia leucotretra, in particular in larvae of Cryptophlebia leucotretra Meyr. To date no pathogenicity with respect to CpGV has been known for the latter species.

The process according to the invention is carried out under non-semisterile, i.e. normal hygienic conditions. The temperatures chosen for growing the Tortricidae larvae are higher than the temperatures customary for the known processes for propagating CpGV. In this way it is possible considerably to shorten the process for producing CpGV.

Olethreutinae species are propagated on a semisynthetic nutrient medium composed of a carbon source, such as corn or bean flour, a source of proteins, vitamins and trace elements, such as wheatgerm and brewer's or feed yeast, ascorbic acid, fungistatics and gelling agents and/or water-binding substances such as agar-agar at 20° to 34° C., preferably at 26° to 30° C. Under these conditions the development of one generation takes 20 to 50 days.

The larvae are infected with CpGV in early larval stages, preferably in the second or third stage, by contamination of the surface of the nutrient medium. The insect larvae are then maintained at the abovementioned temperatures. 5 to 14 days, preferably 6 to 9 days, after the infection the virus-containing cadavers are worked up, and the CpGV is isolated therefrom in known manner.

The invention is illustrated in detail by the example which follows.

Production of CpGV in Cryptophlebia leucotretra

Freshly hatched C. leucotretra moths (sex ratio about 1:1) were transferred into egg-laying cages which were lined with foam and whose upoer opening is covered with transparent film. The moths deposit eggs on the transparent film, which is changed each day. The food used for the moths was water, and yeast extract was added in some instances. The incubation temperature was 24° to 30° C.

Of the larvae hatching from the eggs, each 100 larvae were placed on 200 ml of a semisynthetic nutrient medium composed of 20 g of agar-agar, 140 g of corn middlings, 35 g of wheatgerm, 38 g of brewer's yeast, 5 g of ascorbic acid, 2.3 g of benzoic acid, 1.8 g of p-hydroxybenzoic acid and 760 g of water per kg of medium. After 6 days at an incubation temperature of 28° C., at the time when the larvae were at the end of the second and the start of the third larval stage, the surface of the nutrient medium was contaminated with a granulosis virus suspension. The concentration was adjusted to $2.5 \times 10^6$ viruses/cm². After a further 6 to 9 days, the virus-containing cadavers were aspirated out of the nutrient medium, and the granules were purified by differential centrifugation. The yield was 1.0 to $1.2 \times 10^{12}$ virus particles (granules) per 200 ml of medium.

We claim:

1. A process for growing Cydia pomonella granulosis virus (CpGV), which comprises propagating the virus in larvae of Tortricidae species which have a $LD_{50}$ for this virus which is a factor of 5 to 100,000 higher than that of codling moth larvae.

2. The process as claimed in claim 1, which is carried out in larvae of Tortricidae species which have a $LD_{50}$ which is a factor of 10 to 5,000 higher than that of codling moth larvae.

3. The process as claimed in claim 1, which is carried out in larvae of the subfamily Olethreutinae.

4. The process as claimed in claim 1, which is carried out in larvae of Grapholita molesta, Rhyacionia buoliana, Cydia nigricana or Cryptophlebia leucotretra.

5. The process as claimed in claim 1, which is carried out in larvae of Cryptophlebia leucotretra.

* * * * *